US012773094B2

(12) United States Patent
Tanaka et al.

(10) Patent No.: US 12,773,094 B2
(45) Date of Patent: Oct. 27, 2026

(54) ENDOSCOPE

(71) Applicant: FUJIFILM Corporation, Tokyo (JP)

(72) Inventors: Kunihiko Tanaka, Kanagawa (JP); Shintaro Hattori, Kanagawa (JP); Yutaka Senda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 325 days.

(21) Appl. No.: 18/057,141

(22) Filed: Nov. 18, 2022

(65) Prior Publication Data

US 2023/0165437 A1 Jun. 1, 2023

(30) Foreign Application Priority Data

Nov. 30, 2021 (JP) ................................ 2021-194570

(51) Int. Cl.
*A61B 1/00* (2006.01)
*A61B 1/05* (2006.01)

(52) U.S. Cl.
CPC ...... *A61B 1/00066* (2013.01); *A61B 1/00042* (2022.02); *A61B 1/00179* (2013.01); *A61B 1/05* (2013.01)

(58) Field of Classification Search
CPC ........................ A61B 1/00066; A61B 1/00183
USPC .......................................................... 600/131
See application file for complete search history.

(56) References Cited

U.S. PATENT DOCUMENTS 5,621,830 A * 4/1997 Lucey .................... A61B 1/317 600/137
5,954,654 A 9/1999 Eaton et al.
6,464,645 B1 10/2002 Park et al.
D474,276 S 5/2003 Greise et al.
D501,864 S 2/2005 Greise et al.
D549,332 S 8/2007 Matsumoto et al.
D634,427 S 3/2011 Nishimura
D692,134 S * 10/2013 Lee-Sepsick ................ D24/146
D698,441 S 1/2014 Meguro et al.
D701,603 S 3/2014 Tanaka (Continued)

FOREIGN PATENT DOCUMENTS

CN 102711584 A 10/2012
CN 102802491 A 11/2012

(Continued)

OTHER PUBLICATIONS

"Notification" Office Action issued in JP D2021-026331; mailed by the Japanese Patent Office on Apr. 20, 2022.

(Continued)

*Primary Examiner* — Alexandra L Newton
(74) *Attorney, Agent, or Firm* — Studebaker Brackett PLLC

(57) ABSTRACT

There is provided an endoscope of which operability in changing a visual field direction can be improved.

A grip part includes a first flat surface portion that is formed on a part of an outer surface of the grip part and that is parallel to a direction of an insertion axis, a knob includes a finger placing portion and a pair of finger rest portions, and the finger placing portion is provided at a position facing the first flat surface portion in the direction of the insertion axis in a case where the knob is positioned at a reference position used as a reference of a position relative to the grip part in the direction around the axis.

13 Claims, 10 Drawing Sheets

(56) References Cited

U.S. PATENT DOCUMENTS

| | | | |
|---|---|---|---|
| D795,424 S | 8/2017 | Sloss | |
| D822,218 S | 7/2018 | Asai et al. | |
| D841,160 S | 2/2019 | Cranfield et al. | |
| D852,358 S | 6/2019 | Matuschek et al. | |
| D855,803 S | 8/2019 | Dejima et al. | |
| D874,647 S | 2/2020 | Cranfield et al. | |
| D936,221 S | 11/2021 | Jensen et al. | |
| D956,972 S | 7/2022 | Costin | |
| D1,066,660 S | 3/2025 | Furuta | |
| 2011/0230711 A1 | 9/2011 | Kano et al. | |
| 2012/0165605 A1 | 6/2012 | Yamazaki | |
| 2013/0158429 A1 | 6/2013 | Lee-Sepsick et al. | |
| 2014/0288369 A1 | 9/2014 | Henley et al. | |
| 2016/0345804 A1 | 12/2016 | Wieters et al. | |
| 2017/0354319 A1 | 12/2017 | Sato et al. | |
| 2018/0011308 A1 | 1/2018 | Zhao | |
| 2019/0298321 A1 | 10/2019 | Intintoli et al. | |
| 2019/0374751 A1* | 12/2019 | Finson ............ | A61M 25/10182 |
| 2020/0187759 A1 | 6/2020 | Yamada et al. | |
| 2020/0355907 A1 | 11/2020 | Wieters | |
| 2021/0052152 A1 | 2/2021 | Ochi et al. | |

FOREIGN PATENT DOCUMENTS

| | | | |
|---|---|---|---|
| CN | 105338883 | A | 2/2016 |
| CN | 106030350 | A | 10/2016 |
| CN | 107249428 | A | 10/2017 |
| CN | 112601571 | A | 4/2021 |
| CN | 113243882 | A | 8/2021 |
| EM | 000745963-0006 | | 7/2007 |
| JP | H10-328126 | A | 12/1998 |
| JP | 2005-160789 | A | 6/2005 |
| JP | 1268429 | S | 4/2006 |
| JP | 2008-104732 | A | 5/2008 |
| JP | 1476736 | S | 8/2013 |
| JP | 2015-504709 | A | 2/2015 |
| JP | 2015-131027 | A | 7/2015 |
| JP | 2016-518880 | A | 6/2016 |
| JP | 2017-510327 | A | 4/2017 |
| JP | 1577797 | S | 6/2017 |
| JP | 2018-032014 | A | 3/2018 |
| JP | 2021-510103 | A | 4/2021 |
| WO | 2011/114601 | A1 | 9/2011 |
| WO | 2016/103805 | A1 | 6/2016 |
| WO | 2018/021583 | A1 | 2/2018 |

OTHER PUBLICATIONS

"Notification" Office Action issued in JP D2021-026332; mailed by the Japanese Patent Office on Apr. 20, 2022.

Virtual Expo Group, Indicated in Homepage [https://www.medicalexpo.com/ja/prod/srs-medical/product-81132-513956.html], Dec. 23, 2020, Japan Patent Office, Design Division Official Gazette No. RJ02061968.

An Office Action; "Notice of Reasons for Refusal," mailed by the Japanese Patent Office on Apr. 30, 2025, which corresponds to Japanese Patent Application No. 2021-194570; with English language translation.

An Office Action; "Notice of Reasons for Refusal," mailed by the Japanese Patent Office on Apr. 30, 2025, which corresponds to Japanese Patent Application No. 2021-194571; with English language translation.

An Office Action; mailed by the United States Patent and Trademark Office on Feb. 21, 2025, which corresponds to U.S. Appl. No. 18/057,151 and is related to U.S. Appl. No. 18/057,141.

An Office Action mailed by the United States Patent and Trademark Office on Sep. 11, 2025, which corresponds to U.S. Appl. No. 18/057,151 and is related to U.S. Appl. No. 18/057,141.

An Office Action; "Notice of Reasons for Refusal," mailed by the Japanese Patent Office on Jul. 15, 2025, which corresponds to Japanese Patent Application No. 2021-194570.

An Office Action mailed by China National Intellectual Property Administration on Aug. 26, 2025, which corresponds to Chinese Patent Application No. 202211431214.5; with English language translation.

An Office Action mailed by China National Intellectual Property Administration on Aug. 25, 2025, which corresponds to Chinese Patent Application No. 202211430262.2; with English language translation.

An Office Action mailed by the United States Patent and Trademark Office on Jan. 20, 2026, which corresponds to U.S. Appl. No. 18/057,151 and is related to U.S. Appl. No. 18/057,141.

Office Action issued in CN 202211430262.2; mailed by the State Intellectual Property Office of the People's Republic of China on Mar. 20, 2026.

Office Action issued in CN 202211431214.5; mailed by the State Intellectual Property Office of the People's Republic of China on Mar. 21, 2026.

An Office Action mailed by the United States Patent and Trademark Office on Mar. 26, 2026, which corresponds to U.S. Appl. No. 29/840,411 and is related to U.S. Appl. No. 18/057,141.

"Rejection Decision"; mailed by the China National Intellectual Property Administration of the People's Republic of China on Jun. 18, 2026, which corresponds to Chinese Patent Application No. 202211430262.2.

An Office Action; mailed by the United States Patent and Trademark Office on Jun. 9, 2026, which corresponds to U. S. U.S. Appl. No. 18/057,151.

* cited by examiner

ENDOSCOPE

CROSS-REFERENCE TO RELATED APPLICATION

The present application claims priority under 35 U.S.C § 119(a) to Japanese Patent Application No. 2021-194570 filed on Nov. 30, 2021, which is hereby expressly incorporated by reference, in its entirety, into the present application.

BACKGROUND OF THE INVENTION

1. Field of the Invention

The present invention relates to an endoscope including an insertion unit.

2. Description of the Related Art

A rigid endoscope is known as an endoscope used for endoscopic surgery or the like. Further, an oblique-viewing endoscope of which a diagonal front side with respect to an insertion axis of an insertion unit corresponds to a visual field direction (observation direction) is known as this rigid endoscope. The oblique-viewing endoscope comprises an insertion unit that is to be inserted into an object to be examined and an operation unit that is connected to a proximal end side of the insertion unit. JP2018-32014A discloses such an oblique-viewing endoscope of which the visual field direction can be changed.

The oblique-viewing endoscope disclosed in JP2018-32014A includes an endoscope shaft, a proximal handle, and a rotary wheel. An optical system is disposed at a distal end of the endoscope shaft. In a case where a visual field direction is to be changed, a user rotates the endoscope shaft in a direction around an axis using the proximal handle in a state where the user grips the rotary wheel to hold a horizontal position of a displayed image. Accordingly, the visual field direction of the optical system is rotated about the axis of the endoscope shaft.

SUMMARY OF THE INVENTION

However, in the oblique-viewing endoscope disclosed in JP2018-32014A, in order to rotate the endoscope shaft (insertion unit) in the direction around the axis, as an operation for changing the visual field direction, a user should rotationally operate the proximal handle with a right hand in a state where the user grips the rotary wheel (grip part) provided on a distal end side of the proximal handle (rotational operation member) with, for example, a left hand. Since both hands should be used, there is a problem in that it is difficult to operate the oblique-viewing endoscope.

The present invention has been made in consideration of such circumstances, and an object of the present invention is to provide an endoscope of which operability in changing a visual field direction can be improved.

In order to achieve the object of the present invention, an endoscope according to an aspect of the present invention comprises an insertion unit that is provided with an optical system at a distal end thereof and that is rotatable in a direction around an insertion axis and an operation unit that is connected to a proximal end side of the insertion unit, in which the operation unit includes a grip part that extends in a direction of the insertion axis and a rotational operation member that is provided between the grip part and the insertion unit, is adapted to be rotatable relative to the grip part, and rotates the insertion unit in the direction around the insertion axis, the grip part includes a first flat surface portion that is formed along the insertion axis on a part of an outer surface of the grip part, the rotational operation member includes a finger placing portion on which a finger is placeable and a pair of finger rest portions that is provided on both sides of the finger placing portion in the direction around the insertion axis, and the finger placing portion is provided at a position facing the first flat surface portion in the direction of the insertion axis in a case where the rotational operation member is positioned at a reference position used as a reference of a position relative to the grip part in the direction around the insertion axis.

According to the aspect of the present invention, it is preferable that the first flat surface portion is formed over a proximal end portion from a distal end portion of the grip part in the direction of the insertion axis.

According to the aspect of the present invention, it is preferable that the first flat surface portion includes a first index, the finger placing portion includes a second index, and the first index and the second index are provided on a same line extending in the direction of the insertion axis in a case where the rotational operation member is positioned at the reference position.

According to the aspect of the present invention, it is preferable that the first index and the second index are convex portions.

According to the aspect of the present invention, it is preferable that the convex portion is a convex stripe portion formed along the same line.

According to the aspect of the present invention, it is preferable that the grip part includes a second flat surface portion parallel to the first flat surface portion and formed on the outer surface of the grip part at a position on a side opposite to the first flat surface portion with the insertion axis interposed between the first flat surface portion and the second flat surface portion.

According to the aspect of the present invention, it is preferable that the rotational operation member includes a third index formed at a position different from a position of the second index and indicating a position relative to the grip part in the direction around the insertion axis.

According to the aspect of the present invention, it is preferable that the third index is a concave portion.

According to the aspect of the present invention, it is preferable that the concave portion is a concave stripe portion formed in the direction of the insertion axis.

According to the aspect of the present invention, it is preferable that the rotational operation member is adapted to be rotatable between a first rotational position and a second rotational position relative to the grip part in the direction around the insertion axis, and the reference position is a middle position between the first rotational position and the second rotational position.

According to the aspect of the present invention, it is preferable that the insertion unit includes an image pickup unit that picks up an image of light passing through the optical system, and, in a case where a direction which indicates a top and a bottom of an image formed from image pickup signals output from the image pickup unit, among directions perpendicular to the direction of the insertion axis, is defined as a vertical direction, the first flat surface portion is formed as a surface perpendicular to the vertical direction at a position indicating a top side in the vertical direction on the outer surface of the grip part.

According to the aspect of the present invention, it is preferable that the insertion unit includes an image pickup unit that picks up an image of light passing through the optical system, an image pickup direction of the image pickup unit is a direction inclined with respect to the insertion axis, and the image pickup direction of the image pickup unit includes a component corresponding to a direction that faces a side opposite to a normal direction to the first flat surface portion in a case where the rotational operation member is positioned at the reference position.

According to the aspect of the present invention, it is preferable that the insertion unit includes an outer pipe, a protection sheath that is inserted into the outer pipe, is provided with the optical system at a distal end thereof, and is rotatable integrally with the outer pipe in the direction around the insertion axis of the insertion unit, and an inner sheath that is inserted into the protection sheath, is provided with an image pickup unit, which picks up an image of light passing through the optical system, at a distal end thereof, and is rotatable relative to the protection sheath in the direction around the insertion axis.

According to the present invention, it is possible to improve operability in changing a visual field direction.

DESCRIPTION OF THE PREFERRED EMBODIMENTS

Figure 1:
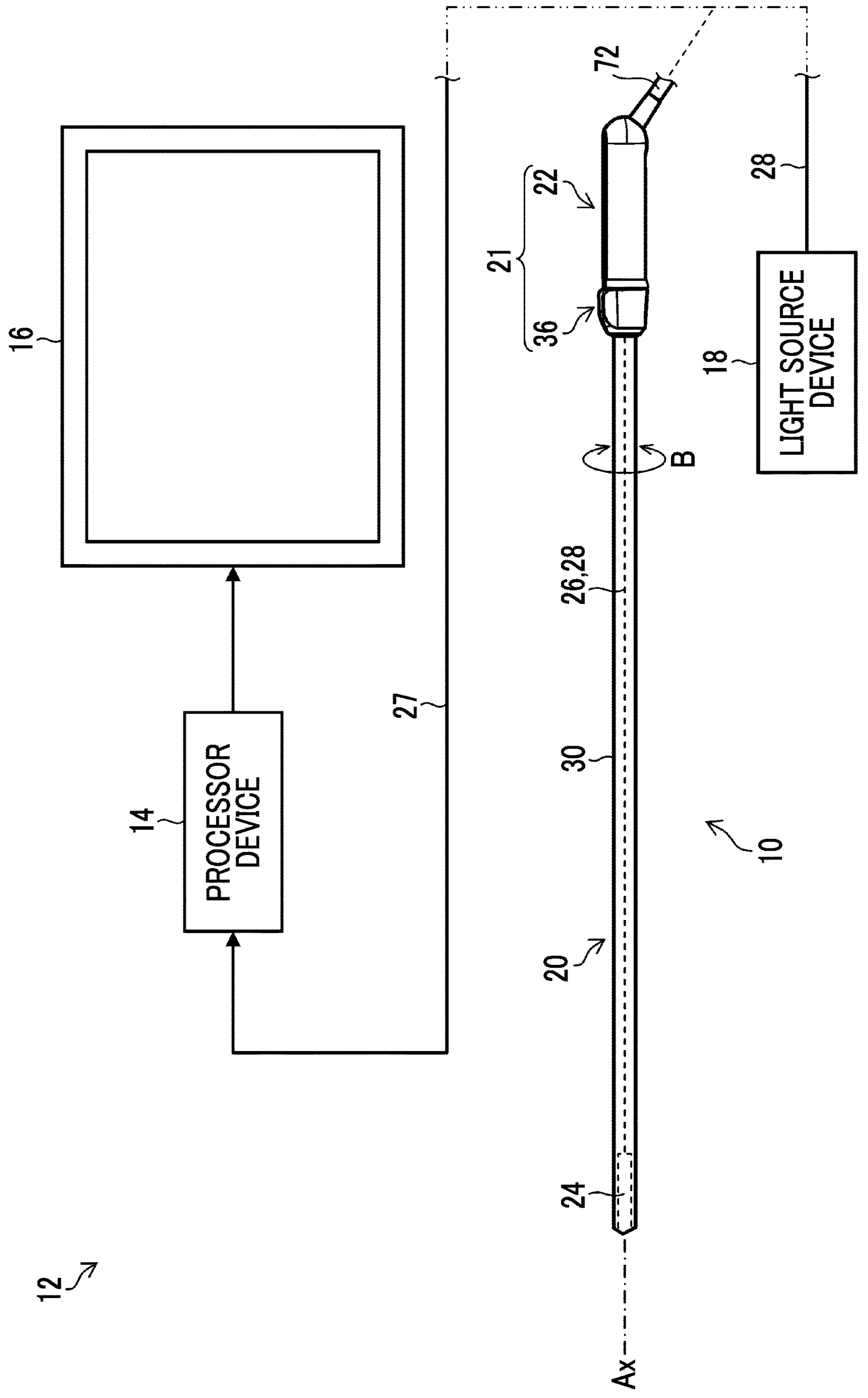
FIG. 1 is a diagram showing a configuration of an endoscope system that comprises an oblique-viewing endoscope.

FIG. 1 is a diagram showing the configuration of an endoscope system 12 that comprises an oblique-viewing endoscope 10. As shown in FIG. 1, the endoscope system 12 comprises the oblique-viewing endoscope 10, a processor device 14, a monitor 16, and a light source device 18. The oblique-viewing endoscope 10 is an example of an endoscope of the present invention.

The oblique-viewing endoscope 10 is a so-called rigid endoscope, and comprises an insertion unit 20 and an operation unit 21 that is connected to a proximal end side of the insertion unit 20. The insertion unit 20 is an example of an insertion unit of the present invention, and the operation unit 21 is an example of an operation unit of the present invention. The insertion unit 20 is formed in a tubular shape (the shape of a pipe), and is to be inserted into a patient's body. The insertion unit 20 has a distal end, a proximal end, and an insertion axis Ax, and an outer peripheral wall of the insertion unit 20 is formed by an outer pipe 30 to be described later. A camera unit 24 to be described later is provided in a distal end portion of the insertion unit 20. Further, a first signal cable 26 and a light guide 28 are inserted into the insertion unit 20.

The first signal cable 26 connects the camera unit 24 to the processor device 14 together with a second signal cable 27 to be described later. A distal end portion of the first signal cable 26 is connected to the camera unit 24, and a proximal end portion of the first signal cable 26 is connected to a distal end portion of the second signal cable 27 in the operation unit 21. A distal end portion (light emitting end surface) of the light guide 28 is provided on a distal end surface of the insertion unit 20, and a proximal end portion (light incident end surface) thereof is connected to the light source device 18. In this embodiment, a multi-core cable in which a plurality of strands (signal lines) are bundled, a shield conductor is provided around the strands, and the strands and the shield conductor are housed in a tubular sheath is exemplified as each of the first signal cable 26 and the second signal cable 27.

The light guide 28 has a light emitting end 28C (see FIG. 2) on a distal end side thereof, and the light emitting end 28C is disposed on a distal end side of the outer pipe 30. Further, the light guide 28 has a light incident end (not shown) on a proximal end side thereof, and the light incident end is connected to the light source device 18. For example, one optical cable in which a plurality of optical fibers are bundled is employed as the light guide 28, and has flexibility.

The operation unit 21 is connected to the proximal end side of the insertion unit 20. The operation unit 21 is gripped by a practitioner during an operation of the oblique-viewing endoscope 10, and receives a rotating operation for rotating a visual field direction of the oblique-viewing endoscope 10 (an observation direction, an image pickup direction, see an optical axis OA shown in FIG. 2) in a direction B around the insertion axis Ax, that is, a circumferential direction of the insertion unit 20 and of the operation unit 21, from the practitioner. The operation unit 21 includes a pipe-like grip part 22 that is gripped by the practitioner and a tubular (annular) knob 36 that receives a rotating operation for rotating the visual field direction. The grip part 22 is an example of a grip part of the present invention, and the knob 36 is an example of a rotational operation member of the present invention. The specific forms of the grip part 22 and the knob 36 in consideration of operability will be described later.

The grip part 22 extends from the proximal end side of the insertion unit 20 in the direction of the insertion axis Ax, and the outer pipe 30 is supported at a distal end portion of the grip part 22 to be rotatable in the direction B around the axis. The grip part 22 of this embodiment has a size that fits the practitioner's hand, and is made of a rubber material or a resin material that withstands autoclave sterilization. Examples of such a rubber material include silicone rubber, fluororubber, and the like. Further, examples of the resin material include polyphenylsulfone (PPSU), poly ether ether ketone (PEEK), and the like. Accordingly, the grip part 22 is less likely to slip in the hand, that is, is less likely to rotate in the direction B around the axis as compared to a case where the grip part 22 is made of a metal material.

The knob 36 is provided between the grip part 22 and the insertion unit 20, and is fixed to a proximal end side of the outer pipe 30. The knob 36 is adapted to be rotatable relative to the grip part 22, and the outer pipe 30 can be rotated relative to the grip part 22 in the direction B around the axis. In a case where the outer pipe 30 is operated to rotate by the knob 36, the visual field direction of the oblique-viewing endoscope 10 (the observation direction, the image pickup direction, see the optical axis OA shown in FIG. 2) can be rotated in the direction B around the axis.

As described in detail later, the grip part 22 includes an airtight space and a non-airtight space therein, and a proximal end side of the first signal cable 26 and a distal end side of the second signal cable 27 are connected to each other at a boundary between both the spaces (see FIG. 3). Accordingly, the camera unit 24 and the processor device 14 are electrically connected to each other via the first signal cable 26 and the second signal cable 27.

The processor device 14 generates an observation image (video) of the inside of the patient's body on the basis of image pickup signals, which are input from the camera unit 24 through the first signal cable 26 and the second signal cable 27, and causes the monitor 16 to display this observation image.

The light source device 18 supplies illumination light to the light guide 28. Accordingly, illumination light is emitted from the light emitting end 28C (see FIG. 2) of the light guide 28 that is provided on the distal end side of the outer pipe 30.

Figure 2:
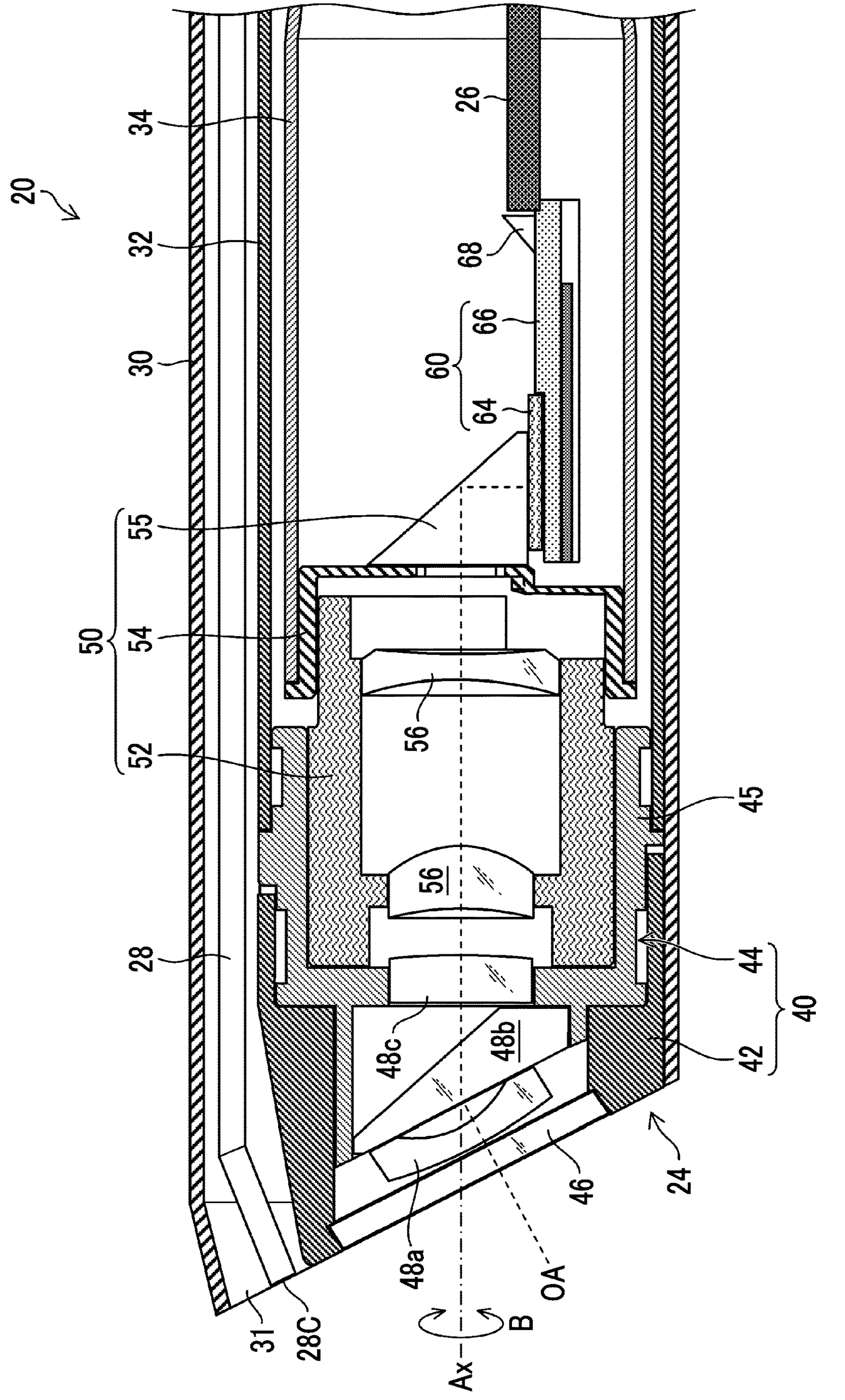
FIG. 2 is an enlarged cross-sectional view of a distal end portion of an insertion unit.

FIG. 2 is an enlarged cross-sectional view of the distal end portion of the insertion unit 20. As shown in FIG. 2, the insertion unit 20 comprises the outer pipe 30, a protection sheath 32, and an inner sheath 34 that are formed substantially in the shape of a pipe parallel to the insertion axis Ax. The outer pipe 30 forms the outer peripheral wall of the insertion unit 20. A distal end-side opening of the outer pipe 30 is inclined from a posture perpendicular to the insertion axis Ax. The outer pipe 30 is an example of an outer pipe of the present invention.

The protection sheath 32 is inserted into and disposed in the outer pipe 30. A distal end optical system 40 of the camera unit 24 is provided on a distal end side of the protection sheath 32. Further, as described in detail later, a proximal end side of the protection sheath 32 is connected to a pipe-like case 74 (see FIG. 3) in the grip part 22 (see FIG. 3). Furthermore, a space 31 in which the light guide 28 is to be disposed is formed between an inner peripheral surface of the outer pipe 30 and an outer peripheral surface of the protection sheath 32. The light guide 28 is inserted into the space 31 and is fixed to the inner peripheral surface of the outer pipe 30 and to the outer peripheral surface of the protection sheath 32. The protection sheath 32 is an example of a protection sheath of the present invention.

The inner sheath 34 is inserted into and disposed in the protection sheath 32. The first signal cable 26 is inserted into the inner sheath 34. A proximal end optical system 50 and an image pickup unit 60 of the camera unit 24 are provided on a distal end side of the inner sheath 34. Further, as described in detail later, a proximal end side of the inner sheath 34 is connected to a connection member 90 (see FIG. 3) in the grip part 22 (see FIG. 3). The inner sheath 34 is an example of an inner sheath of the present invention.

As shown in FIG. 2, the camera unit 24 comprises the distal end optical system 40, the proximal end optical system 50, and the image pickup unit 60. Reference character OA shown in FIG. 2 denotes the optical axis of the optical system (an objective lens 48*a* to be described later) of the camera unit 24, and indicates the image pickup direction of the image pickup unit 60. The optical axis OA is set to a direction inclined with respect to the insertion axis Ax.

The distal end optical system 40 is provided on the distal end side of the protection sheath 32. The distal end optical system 40 is an oblique-viewing optical system that refracts light, which is incident in a direction inclined with respect to the insertion axis Ax, in a direction parallel to the insertion axis Ax and guides the light to the proximal end optical system 50. The distal end optical system 40 includes a distal end portion body 42 and a distal end lens barrel 44 that is provided in the distal end portion body 42. The distal end optical system 40 is an example of an optical system of the present invention.

The distal end portion body 42 forms the distal end portion of the insertion unit 20 (protection sheath 32) and is a cap that covers the distal end lens barrel 44. Further, the distal end portion body 42 is formed substantially in the shape of a pipe parallel to the insertion axis Ax. Furthermore, a cover glass 46, which is in an inclined posture corresponding to an inclination angle of an objective lens 48*a* provided in the distal end lens barrel 44, is provided at a distal end-side opening portion of the distal end portion body 42.

Further, the distal end portion body 42 is fixed to the inner peripheral surface of the outer pipe 30. Accordingly, in a case where the outer pipe 30 is rotated in the direction B around the axis, the distal end optical system 40 and the protection sheath 32 are integrally rotated in the direction B around the axis together with the outer pipe 30.

The objective lens 48*a*, a prism 48*b*, and a lens 48*c* are housed in the distal end lens barrel 44. The objective lens 48*a* is inclined from a posture perpendicular to the insertion axis Ax and faces the cover glass 46. The objective lens 48*a* emits light, which is incident through the cover glass 46, toward the prism 48*b*. The prism 48*b* refracts light incident from the objective lens 48*a*, that is, light incident in a direction inclined with respect to the insertion axis Ax in a direction parallel to the insertion axis Ax and then emits the light toward the lens 48*c*. The lens 48*c* is in a posture perpendicular to the insertion axis Ax, and emits light incident from the prism 48*b* toward lenses 56 that are provided in a proximal end lens barrel 52 of the proximal end optical system 50. The configuration of an optical system provided in the distal end lens barrel 44 is not particularly limited as long as light incident in a direction inclined with respect to the insertion axis Ax can be guided into the proximal end lens barrel 52.

A tubular portion 45, which extends toward a proximal end side of the distal end lens barrel 44, is formed at the distal end lens barrel 44. The tubular portion 45 is externally fitted to be rotatable relative to a distal end portion of the proximal end lens barrel 52 in the direction B around the axis. Accordingly, the proximal end lens barrel 52 is fitted to be rotatable relative to the distal end lens barrel 44 in the direction B around the axis.

The proximal end optical system 50 is provided on the distal end side of the inner sheath 34, and guides light, which is incident from the distal end lens barrel 44, to the image pickup unit 60. The proximal end optical system 50 includes the proximal end lens barrel 52, a holder 54, and a prism 55.

A proximal end side of the proximal end lens barrel 52 is fixed to the distal end side of the inner sheath 34 via the holder 54. Further, the distal end side of the proximal end lens barrel 52 is fitted to be rotatable relative to a proximal end-side opening portion of the tubular portion 45 in the direction B around the axis as already described. Accordingly, one of the distal end lens barrel 44 and the proximal end lens barrel 52 is rotatable relative to the other thereof in the direction B around the axis. As a result, the inner sheath 34 inserted into the protection sheath 32 is rotatable relative to the protection sheath 32 in the direction B around the axis.

A plurality of lenses 56 having an optical axis parallel to the insertion axis Ax are provided in the proximal end lens barrel 52. Each lens 56 emits light, which is incident from the distal end lens barrel 44, toward the prism 55.

The holder 54 is formed substantially in the shape of a pipe parallel to the insertion axis Ax, and is fixed to the distal end side of the inner sheath 34. Further, the holder 54 is externally fitted and fixed to the proximal end side of the proximal end lens barrel 52. Accordingly, since the inner sheath 34 and the proximal end lens barrel 52 are connected to each other by the holder 54, the inner sheath 34, the holder 54, and the proximal end lens barrel 52 are integrally rotatable relative to the protection sheath 32 in the direction B around the axis.

The prism 55 is held at a proximal end-side opening portion of the holder 54, and the image pickup unit 60 is held via the prism 55. For this reason, the image pickup unit 60 is rotatable relative to the protection sheath 32 in the direction B around the axis integrally with the inner sheath 34 and the proximal end lens barrel 52 via the prism 55 and the holder 54.

The prism 55 refracts light, which is incident through the proximal end lens barrel 52, by an angle of 90°. A mirror may be used instead of the prism 55.

The image pickup unit 60 picks up the image of the light (observation image) that passes through the distal end optical system 40 and the proximal end optical system 50 and is reflected by the prism 55. The image pickup unit 60 comprises an image pickup element 64 and a circuit board 66. The image pickup unit 60 is an example of an image pickup unit of the present invention.

The image pickup element 64 is fixed to the prism 55 in a state where the image pickup element 64 is mounted on the circuit board 66, and is mounted on the holder 54 via the prism 55. Further, the image pickup element 64 picks up the image of the light, which is refracted by the prism 55, and outputs image pickup signals. A charge coupled device (CCD) image sensor or a complementary metal oxide semiconductor (CMOS) image sensor is used as the image pickup element 64.

The circuit board 66 controls the drive of the image pickup element 64. Further, a distal end side of the first signal cable 26 is connected to the circuit board 66 via a connector 68. Furthermore, the circuit board 66 outputs the image pickup signals of the image pickup element 64 to the first signal cable 26 via the connector 68.

Figure 3:
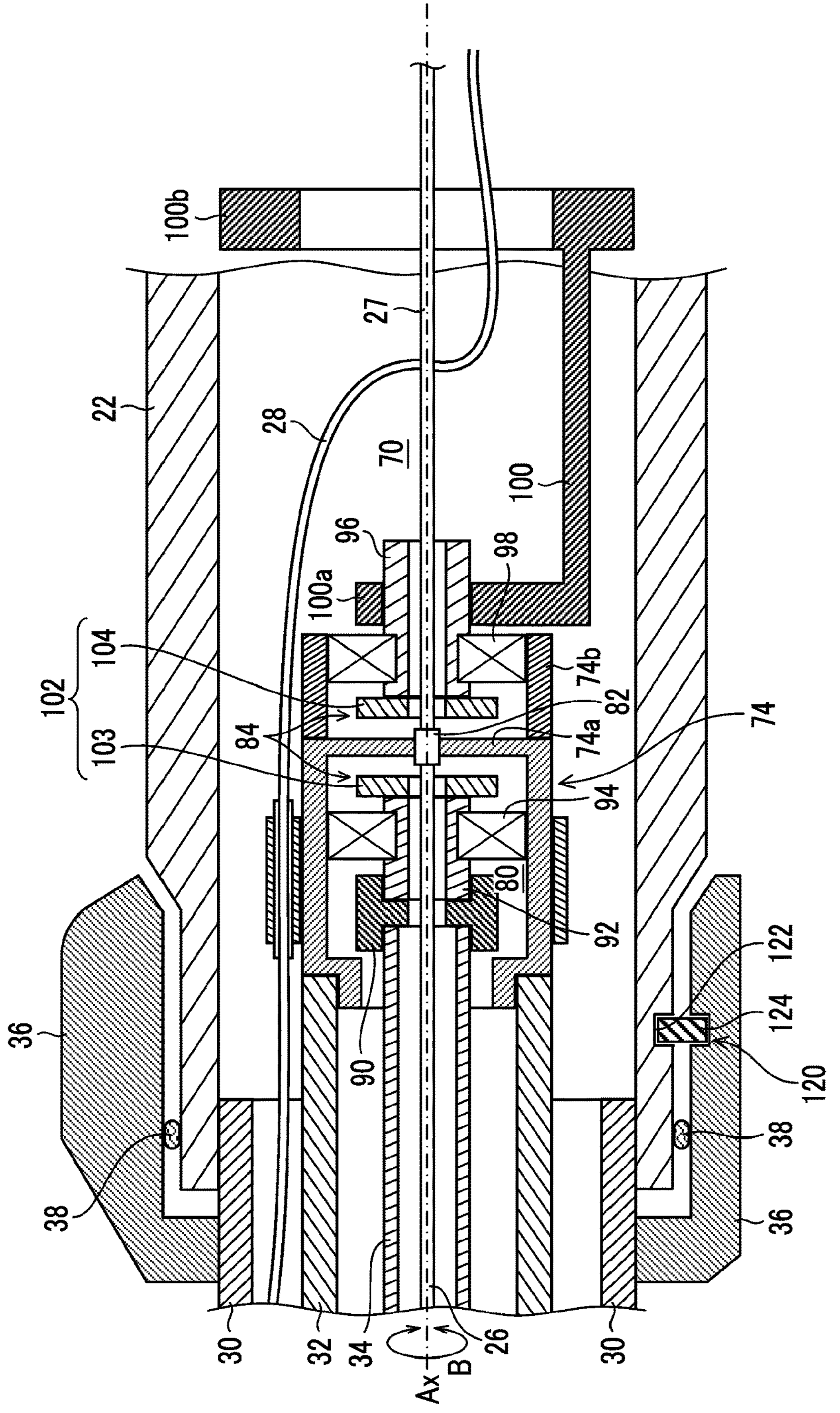
FIG. 3 is a cross-sectional view of a main portion of a grip part.

FIG. 3 is a cross-sectional view of a main portion of the grip part 22. As shown in FIG. 3, the grip part 22 is formed in the shape of a pipe parallel to the insertion axis Ax.

The knob 36 fixed to the proximal end side of the outer pipe 30 is provided on a distal end side of the grip part 22. For example, the knob 36 is rotatably provided on an outer peripheral surface of a distal end portion of the grip part 22 via a seal ring 38. Accordingly, the knob 36 is adapted to be rotatable relative to the grip part 22 in the direction B around the axis. In a case where the knob 36 is operated to rotate in the direction B around the axis, the outer pipe 30 is rotated relative to the grip part 22 in the direction B around the axis, and the protection sheath 32 and the distal end optical system 40 (the distal end portion body 42 and the distal end lens barrel 44, see FIG. 2) are integrally rotated in the same direction via the outer pipe 30. Accordingly, the visual field direction (the observation direction, the image pickup direction) of the oblique-viewing endoscope 10 can be changed.

The proximal end sides of the protection sheath 32 and the inner sheath 34 are inserted into the grip part 22 from a distal end-side opening portion of the grip part 22. Further, a distal end side of an external cable 72 shown in FIG. 1 is connected to a proximal end side of the grip part 22, and the external cable 72 is provided integrally with the grip part 22. Furthermore, the second signal cable 27 and the light guide 28 are inserted into the external cable 72.

Returning to FIG. 3, a light guide-insertion space 70 is formed in the grip part 22. Moreover, the case 74 is provided in the grip part 22. The case 74 is disposed on a distal end side of the light guide-insertion space 70.

Next, a configuration that allows the first signal cable 26 and the second signal cable 27 to be inserted into and disposed in the grip part 22 will be described.

As shown in FIG. 3, the case 74 is formed substantially in the shape of a pipe parallel to the insertion axis Ax to have a diameter smaller than the inner diameter of the grip part 22 and is housed in the grip part 22. The case 74 is supported in an internal space of the grip part 22 by the protection sheath 32 and the external cable 72 (see FIG. 1), and the like. A distal end side of the case 74 is connected to a proximal end portion of the protection sheath 32. Accordingly, in a case where the outer pipe 30 is rotated relative to the grip part 22 in the direction B around the axis, this rotational force is transmitted to the distal end optical system 40, the protection sheath 32, and the case 74. As a result, the case 74 is rotated in the same direction as the outer pipe 30.

The proximal end side of the inner sheath 34 and the proximal end side of the first signal cable 26 are disposed in the case 74. Further, a partition wall **74*a* perpendicular to the insertion axis Ax is provided in the case 74, for example, in a proximal end-side opening portion of the case 74. The partition wall 74*a* closes the proximal end-side opening portion of the case 74**.

Furthermore, a tubular portion **74*b* parallel to the insertion axis Ax is provided on a proximal end side of the case 74. The tubular portion 74*b* is formed to have the same diameter as the case 74, but may be formed to have a diameter different from the diameter of the case 74. Further, the tubular portion 74*b* may be formed integrally with the case 74. In this situation, the proximal end side of the case 74 functions as a tubular portion 74*b*. The distal end side of the second signal cable 27 is disposed in the case 74 and the tubular portion 74*b* in addition to a part of a connecting unit 84** to be described later.

Figure 4:
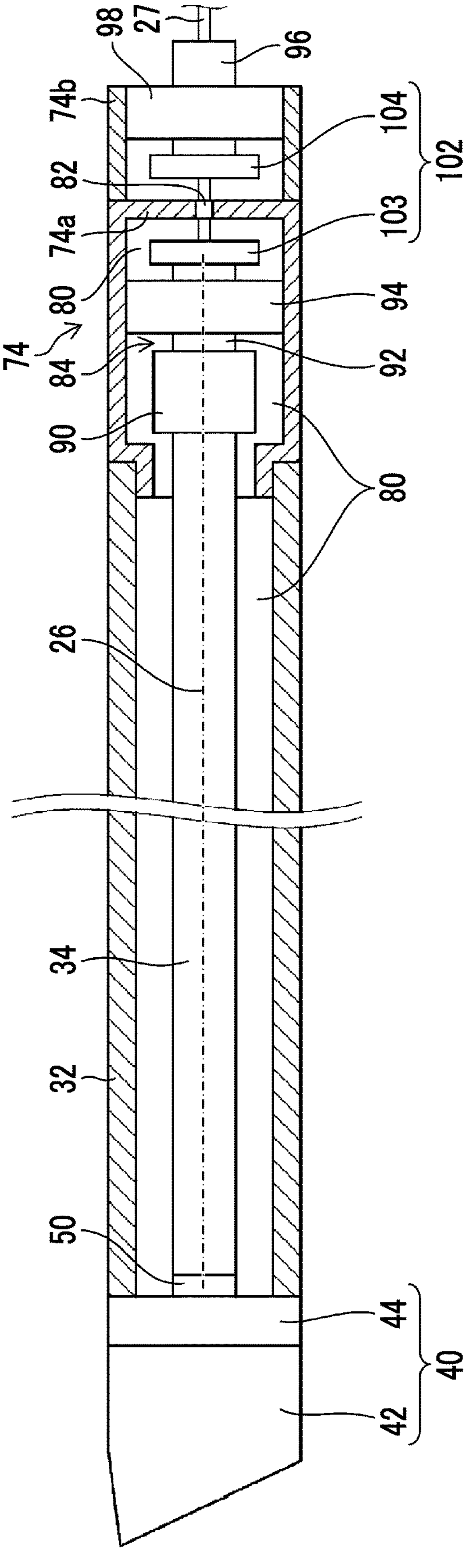
FIG. 4 is a cross-sectional view of a protection sheath and a case.

FIG. 4 is a cross-sectional view of the protection sheath 32 and the case 74. A sealed space 80 (airtight space) is formed in the protection sheath 32 and the case 74 as shown in FIG. 4, and the inner sheath 34, the image pickup unit 60 (see FIG. 2), the first signal cable 26, and the like are disposed in the sealed space 80. A distal end side of the sealed space 80 is defined by the distal end optical system 40. Further, a proximal end side of the sealed space 80 is defined by the partition wall **74*a*. Accordingly, the moisture-proof property of the camera unit 24 (see FIG. 2**) is improved, so that fogging and breakage are prevented.

Figure 5:
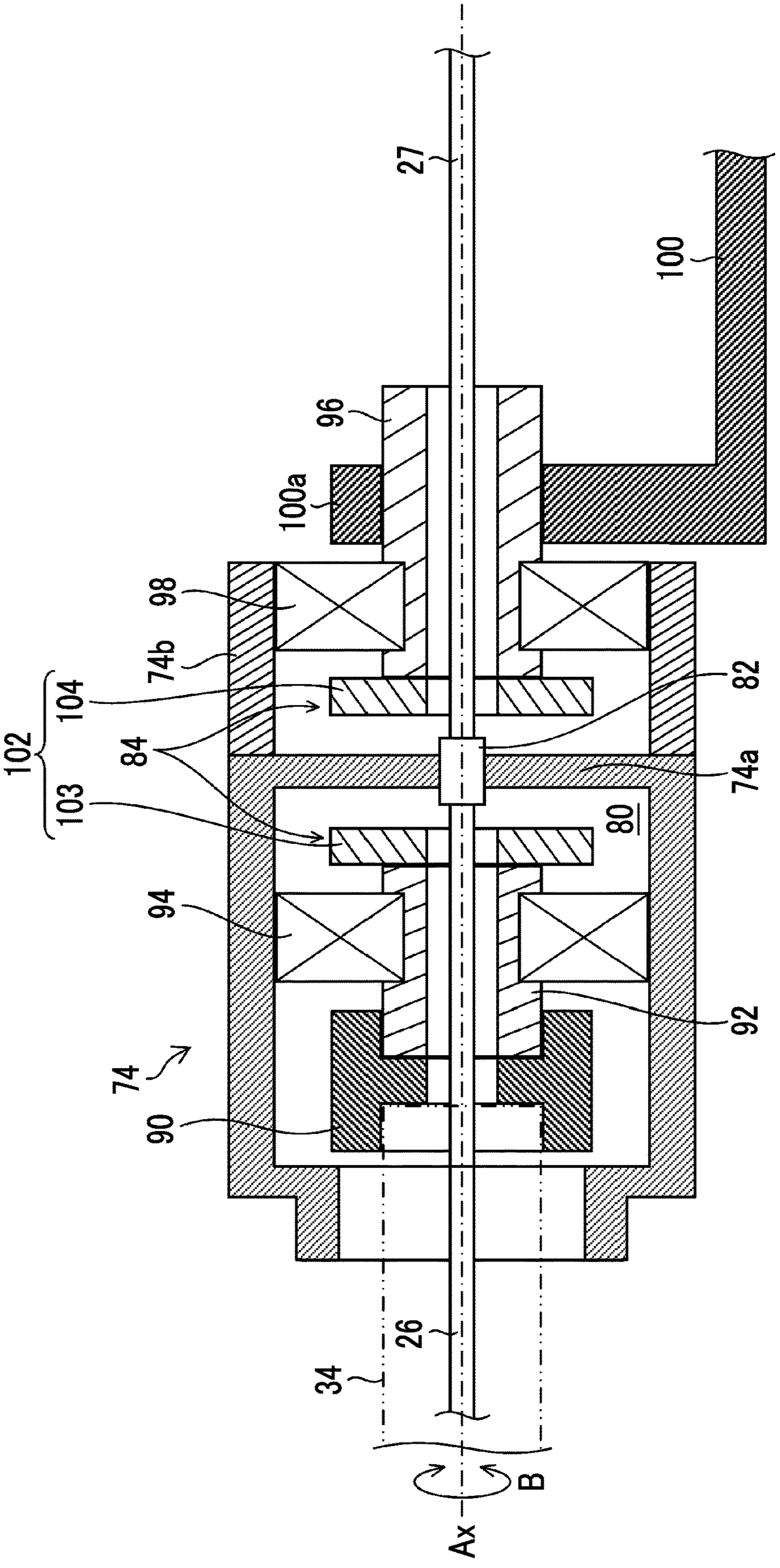
FIG. 5 is an enlarged cross-sectional view of the case and a tubular portion.

FIG. 5 is an enlarged cross-sectional view of the case 74 and the tubular portion **74*b*. As shown in FIGS. 3 to 5, the partition wall 74*a* already described, an airtight connector 82, and a connecting unit 84 are provided in the case 74 and the tubular portion 74*b***.

The airtight connector 82 is provided to pass through the inside and outside of the sealed space 80 and to be rotatable relative to the partition wall **74*a* in the direction B around the axis. The airtight connector 82 electrically connects the proximal end side of the first signal cable 26 provided in the case 74 (in the sealed space 80) to the distal end side of the second signal cable 27 provided in the tubular portion 74***b* (outside the sealed space 80). Accordingly, the first signal cable 26 and the second signal cable 27 are inserted into and disposed in the grip part 22. In a case where the first signal cable 26 and the second signal cable 27 are torsionally deformable in the direction B around the axis, for example, in a case where each of the first signal cable 26 and the second signal cable 27 is formed of a plurality of separated strands, the airtight connector 82 may be fixed to the partition wall 74*a*.

The connecting unit 84 is provided in the case 74 and the tubular portion 74*b* to be rotatable relative to the case 74 and the tubular portion 74*b* in the direction B around the axis. The first signal cable 26 and the second signal cable 27 are inserted into the connecting unit 84. The connecting unit 84 magnetically connects the proximal end side of the inner sheath 34 provided in the case 74 (in the sealed space 80) to a distal end side of the external cable 72 (see FIG. 1) provided outside the sealed space 80 with the partition wall 74*a* interposed therebetween.

The connecting unit 84 comprises a connection member 90, a bearing receiving member 92, and a bearing 94. Further, the connecting unit 84 comprises a bearing receiving member 96, a bearing 98, a connecting beam 100, and a magnet coupling 102 in addition to the above-mentioned members.

The connection member 90 and the bearing receiving member 92 are provided in the case 74 (in the sealed space 80), and are formed substantially in the shape of a pipe parallel to the insertion axis Ax. Further, the first signal cable 26 is inserted into the connection member 90 and the bearing receiving member 92.

The connection member 90 connects the proximal end side of the inner sheath 34 to a distal end side of the bearing receiving member 92 in the case 74 (in the sealed space 80). Accordingly, the distal end side of the bearing receiving member 92 is connected to the proximal end side of the inner sheath 34 via the connection member 90.

The distal end side of the bearing receiving member 92 is connected to the connection member 90 as described above, and a proximal end side thereof is fixed to a first magnet 103 of the magnet coupling 102. Further, the bearing 94, which is to be inscribed in the case 74, is fixed to an outer peripheral surface of the bearing receiving member 92. Accordingly, the bearing receiving member 92 and the first magnet 103 are held in the case 74 to be rotatable relative to the case 74 in the direction B around the axis. Various publicly known radial bearings, such as a ball bearing and a roller bearing, are used as the bearing 94.

The bearing receiving member 96 is provided in the tubular portion 74*b* (outside the sealed space 80). The bearing receiving member 96 is formed substantially in the shape of a pipe parallel to the insertion axis Ax, and the second signal cable 27 is inserted into the bearing receiving member 96.

A distal end portion of the bearing receiving member 96 is fixed to a second magnet 104 of the magnet coupling 102 in the tubular portion 74*b*, and a proximal end portion thereof is connected to the connecting beam 100. Further, the bearing 98, which is to be inscribed in the tubular portion 74*b*, is fixed to an outer peripheral surface of the bearing receiving member 96. Accordingly, the bearing receiving member 96 and the second magnet 104 are held in the tubular portion 74*b* to be rotatable relative to the tubular portion 74*b* in the direction B around the axis. Various publicly known radial bearings are also used as the bearing 98 as in the case of the bearing 94.

As shown in FIG. 3, the connecting beam 100 is formed in the shape of a beam that extends in the direction of the insertion axis Ax in the light guide-insertion space 70. The connecting beam 100 includes a ring portion 100*a* provided on a distal end side thereof and a ring portion 100*b* provided on a proximal end side thereof, the ring portion 100*a* is externally fitted to a proximal end side of the bearing receiving member 96, and the ring portion 100*b* is fixed to the distal end side of the external cable 72 (see FIG. 1). As a result, the second magnet 104 and the external cable 72 (see FIG. 1) are connected to each other via the bearing receiving member 96 and the connecting beam 100.

The magnet coupling 102 includes the first magnet 103 provided in the case 74 (in the sealed space 80) and the second magnet 104 provided in the tubular portion 74*b* (outside the sealed space 80) with the partition wall 74*a* interposed therebetween. The magnet coupling 102 is a magnetic connecting member that magnetically connects the bearing receiving member 92 (inner sheath 34) to the bearing receiving member 96 (external cable 72). Each of the first magnet 103 and the second magnet 104 is formed in the shape of a disk, and a hole is formed at a central portion thereof. The first signal cable 26 is inserted into and disposed in the hole of the first magnet 103, and the second signal cable 27 is inserted into and disposed in the hole of the second magnet 104.

Since the inner sheath 34 and the external cable 72 (see FIG. 1) are magnetically connected to each other via the magnet coupling 102, torque (stop torque, rotational torque) can be transmitted to the inner sheath 34 from the external cable 72 (see FIG. 1). Accordingly, in a case where the practitioner rotationally operates the outer pipe 30 using the knob 36, the rotation (co-rotation) of the protection sheath 32 and the inner sheath 34 (the proximal end optical system 50 and the image pickup unit 60) in the direction B around the axis is prevented. That is, the posture of the inner sheath 34 in the direction B around the axis is maintained by the magnet coupling 102.

Figure 6:
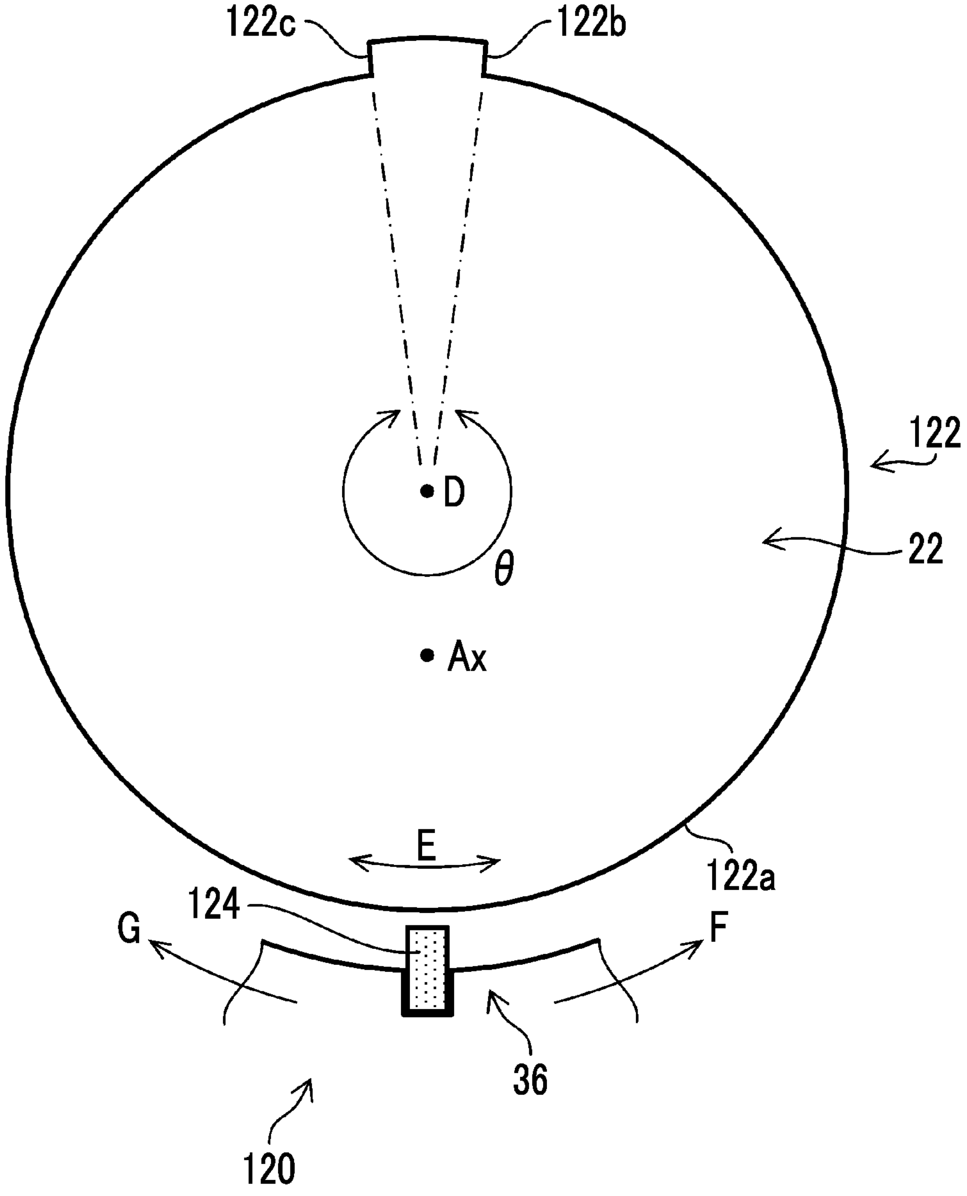
FIG. 6 is a schematic diagram showing a configuration of a rotation stopper.

Next, a rotation stopper 120 (see FIG. 6), which defines (regulates) a rotational operation range of the knob 36 shown in FIG. 1, will be described. FIG. 6 is a schematic diagram showing the configuration of the rotation stopper 120 in a case where the knob 36 is viewed from the proximal end side of the grip part 22. The rotation stopper 120 is also shown in FIG. 3.

As shown in FIG. 6, the rotation stopper 120 includes a stopper groove 122 and a stopper pin 124. The stopper groove 122 is formed on the outer peripheral surface of the distal end portion of the grip part 22. The stopper groove 122 includes a groove portion 122*a*, a wall portion 122*b* that is formed on one end side of the groove portion 122*a*, and a wall portion 122*c* that is formed on the other end side of the groove portion 122*a*. The groove portion 122*a* is formed in an arc shape centered on a central axis D of rotation of the knob 36 relative to the grip part 22 on a plane perpendicular to the insertion axis Ax. Further, each of the wall portions 122*b* and 122*c* is formed as a stopper surface that protrudes from the groove portion 122*a* in a normal direction. On the other hand, the stopper pin 124 protrudes from an inner peripheral surface of the knob 36 toward the central axis D of rotation, and is inserted into the groove portion 122*a*.

According to the rotation stopper 120 shown in FIG. 6, the position of the stopper pin 124 shown by a solid line in FIG. 6 indicates a middle position of a rotational operation range θ (for example, 340°) of the knob 36. In a case where the knob 36 is operated to rotate in a counterclockwise direction F from this middle position, the stopper pin 124 is moved along the groove portion 122*a* in the counterclockwise direction F. In a case where the stopper pin 124 is in contact with the wall portion 122*b*, the rotation of the knob 36 in the counterclockwise direction F is regulated. The position of the knob 36 in this case corresponds to a first rotational position relative to the grip part 22 in the direction B around the axis. Further, in a case where the knob 36 is operated to rotate in a clockwise direction G from the middle position, the stopper pin 124 is moved along the groove portion 122*a* in the clockwise direction G. In a case where the stopper pin 124 is in contact with the wall portion 122*c*, the rotation of the knob 36 in the clockwise direction G is regulated. The position of the knob 36 in this case corresponds to a second rotational position relative to the grip part 22 in the direction B around the axis.

The rotational operation range θ of the knob 36 of the operation unit 21 of this embodiment is defined as an angle of 340° by the rotation stopper 120. As a result, the knob 36 is adapted to be rotatable in each of the counterclockwise direction F and the clockwise direction G from the middle position between the first and second rotational positions by an angle of 170°. The middle position is an example of a reference position of the present invention, that is, a reference position that is used as a reference of the position of the knob 36 relative to the grip part 22 in the direction B around the axis. The reference position is not limited to the middle position, and, for example, a position shifted in each of the counterclockwise direction F or the clockwise direction G from the middle position may be used as the reference position. However, in a case where the middle position is set as the reference position, the practitioner can adjust the visual field direction starting from the middle position as a starting point and can set the image pickup direction of the oblique-viewing endoscope 10 to a diagonally downward direction as described in detail later.

Next, a preferred embodiment in consideration of the operability of the grip part 22 and of the knob 36 will be described with reference to FIGS. 7 to 10. In FIGS. 7 to 10, a description will be made using a three-dimensional Cartesian coordinate system having three directions (an X direction, a Y direction, and a Z direction).

Figure 7:
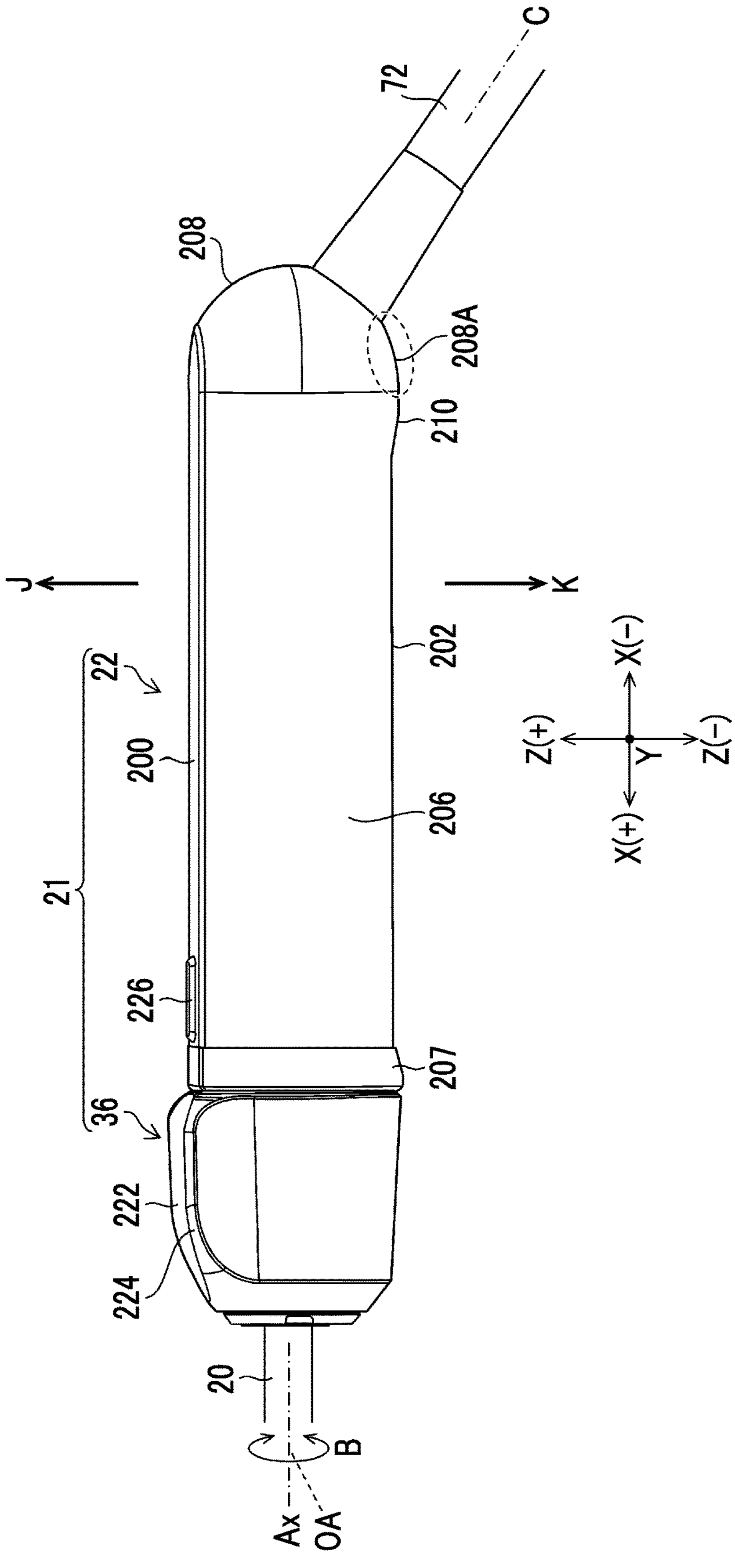
FIG. 7 is a side view of an operation unit in a case where the operation unit is viewed in a Y(+) direction from a Y(−) side.

For example, in a case where the posture of the oblique-viewing endoscope 10 is determined such that the insertion axis Ax is parallel to a horizontal direction and the external cable 72 extends in a diagonally right-downward direction C from a proximal end portion 208 of the grip part 22 as shown in FIG. 7, a direction parallel to the insertion axis Ax is referred to as the X direction, a distal end side in the X direction corresponds to an X(+) direction, and a proximal end side in the X direction corresponds to an X(−) direction. Further, in the posture shown in FIG. 7, a direction perpendicular to a plane of paper of FIG. 7 among directions orthogonal to the insertion axis Ax is referred to as the Y direction, a back side of the plane of paper in the Y direction corresponds to a Y(+) direction, and a front side of the plane of paper in the Y direction corresponds to a Y(−) direction. Furthermore, a direction orthogonal to both the X direction and the Y direction is described as the Z direction, an upper side in the Z direction is described to correspond to a Z(+) direction, and a lower side in the Z direction is described to correspond to a Z(−) direction.

Figure 8:
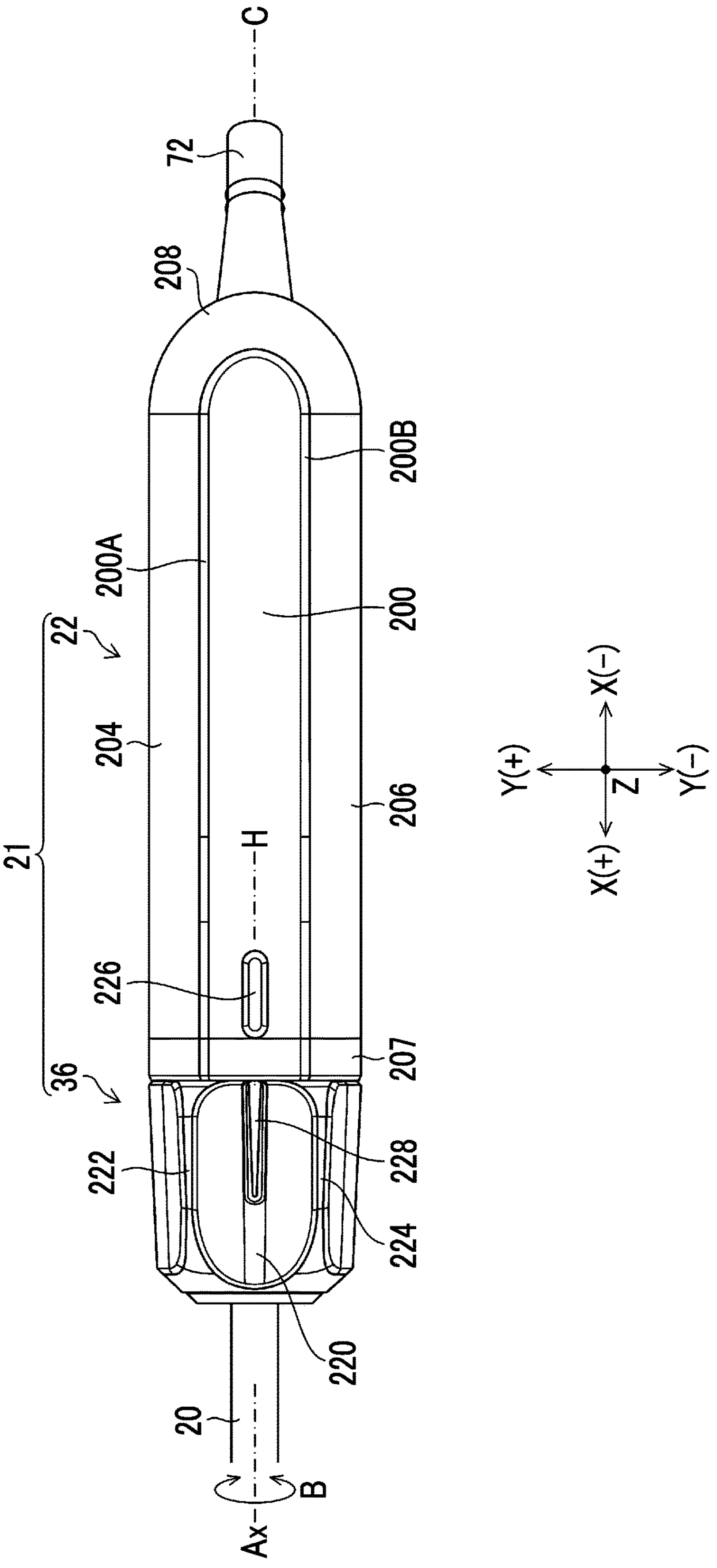
FIG. 8 is a top view of the operation unit in a case where the operation unit is viewed in a Z(−) direction from a Z(+) side.
Figure 9:
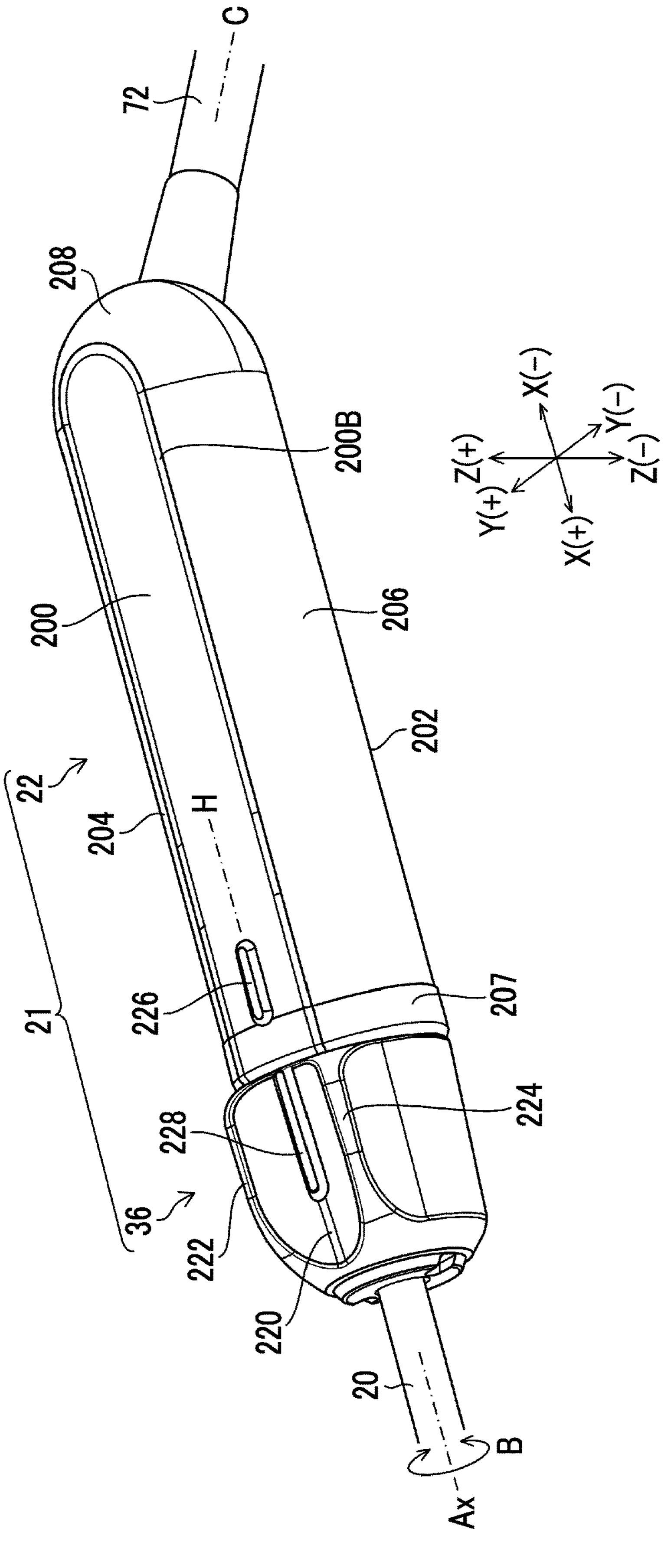
FIG. 9 is a perspective view of the operation unit in a case where the operation unit is viewed in a Z(+) direction.
Figure 10:
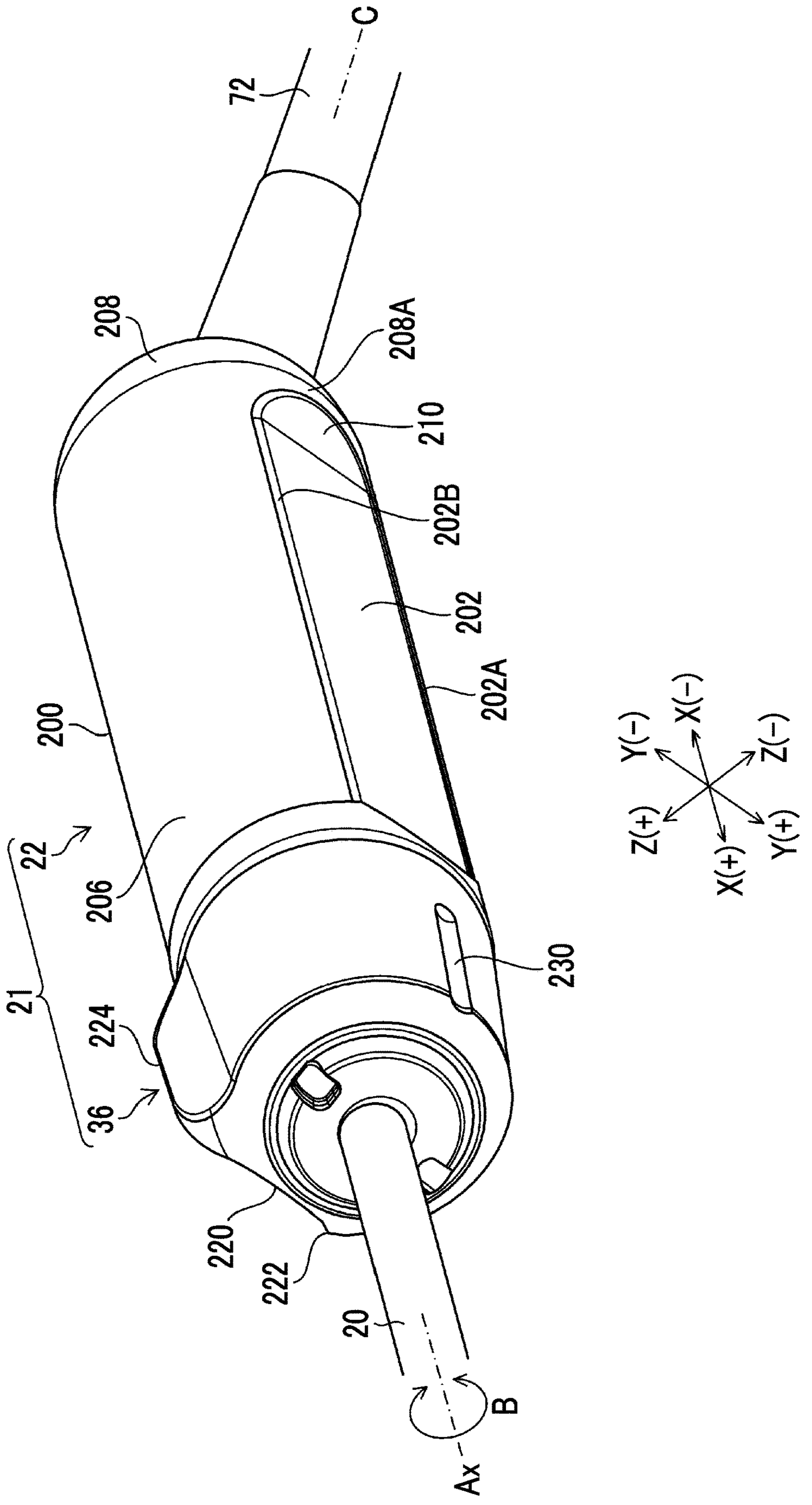
FIG. 10 is a perspective view of the operation unit in a case where the operation unit is viewed from a Z(−) side.

Here, FIG. 7 is a side view of the operation unit 21 in a case where the operation unit 21 is viewed in the Y(+) direction from a Y(−) side. FIG. 8 is a top view of the operation unit 21 in a case where the operation unit 21 is viewed in the Z(−) direction from a Z(+) side. FIG. 9 is a perspective view of the operation unit 21 in a case where the operation unit 21 is viewed in the Z(+) direction. FIG. 10 is a perspective view of the operation unit 21 in a case where the operation unit 21 is viewed from a Z(−) side. With regard to the operation unit 21 shown in FIGS. 7 to 10, a state where the knob 36 is positioned at the middle position (reference position) relative to the grip part 22 is shown.

First, the grip part 22 will be described. As shown in FIGS. 7 to 10, an outer surface of the grip part 22 includes a first flat surface portion 200 (see FIG. 8), a second flat surface portion 202 (see FIG. 10), a first curved surface portion 204 (see FIG. 8), and a second curved surface portion 206 (see FIG. 10).

As shown in FIGS. 7 and 8, the first flat surface portion 200 is a part of the outer surface of the grip part 22 and is formed on a surface, which is positioned on the Z(+) side, of the outer surface of the grip part 22. Further, the first flat surface portion 200 is formed as a surface along the insertion axis Ax, specifically, a surface parallel to the insertion axis Ax. Furthermore, the first flat surface portion 200 is formed over the proximal end portion 208 from a distal end portion 207 of the grip part 22 in the direction of the insertion axis Ax. The first flat surface portion 200 is an example of a first flat surface portion of the present invention. The first flat surface portion 200 functions as a surface with which a base portion of a thumb of the practitioner's hand is to be in contact in a case where the practitioner grips the grip part 22.

Moreover, in a case where a direction which indicates the top and the bottom of a monitor image formed from image pickup signals output from the image pickup unit 60 (see FIG. 3), among directions perpendicular to the direction of the insertion axis, is defined as a vertical direction, the first flat surface portion 200 is formed on the outer surface of the grip part 22 as a surface perpendicular to the vertical direction at a position indicating a top side in the vertical direction. Accordingly, the practitioner can ascertain that a flat surface of the first flat surface portion 200 corresponds to the top side of the monitor image displayed on the monitor 16.

As shown in FIGS. 7 and 10, the second flat surface portion 202 is a part of the outer surface of the grip part 22 and is formed on a surface, which is positioned on the Z(−) side, of the outer surface of the grip part 22. Further, the second flat surface portion 202 is formed as a surface parallel to the first flat surface portion 200 at a position on a side opposite to the first flat surface portion 200 with the insertion axis Ax interposed between the first flat surface portion 200 and the second flat surface portion 202. Furthermore, the second flat surface portion 202 is formed over a position on the front side (X(+) side) of the proximal end portion 208 from the distal end portion 207 of the grip part 22 in the direction of the insertion axis Ax.

Specifically, as shown in FIG. 7, the proximal end portion 208 of the grip part 22 includes a bulging portion 208A that protrudes in a dome shape in the Z(−) direction. A proximal end side (X(−) side) of the second flat surface portion 202 is formed to be connected to an inclined flat surface 210 formed on a distal end side (X(+) side) of the bulging portion 208A. The second flat surface portion 202 is an example of a second flat surface portion of the present invention. The second flat surface portion 202 functions as a surface with which four fingers (particularly, a middle finger and a ring finger) other than the thumb among the practitioner's fingers are to be in contact in a case where the practitioner grips the grip part 22.

As shown in FIG. 8, the first curved surface portion 204 is a curved surface portion that connects a side edge portion 200A of the first flat surface portion 200 positioned on a Y(+) side to a side edge portion 202A (see FIG. 10) of the second flat surface portion 202 (see FIG. 10) positioned on the Y(+) side, and is formed as a curved surface portion bulging on the Y(+) side. The first curved surface portion 204 functions as a surface with which, particularly, a palm of the hand (a concave portion at the center of the palm of the hand) of the palm of the practitioner's hand is to be in contact in a case where the practitioner grips the grip part 22 with, for example, the right hand.

As shown in FIG. 8, the second curved surface portion 206 is a curved surface portion that connects a side edge portion 200B of the first flat surface portion 200 positioned on the Y(−) side to a side edge portion 202B (see FIG. 10) of the second flat surface portion 202 (see FIG. 10) positioned on the Y(−) side, and is formed as a curved surface portion bulging on the Y(−) side. The second curved surface portion 206 functions as a surface with which tips of four fingers (particularly, the middle finger and the ring finger) other than the thumb among the practitioner's fingers are to be in contact in a case where the practitioner grips the grip part 22 with, for example, the right hand.

According to the grip part 22 having such a configuration, since the grip part 22 includes the first flat surface portion 200, it is easy for the practitioner to grip the grip part 22. Further, since the grip part 22 includes the second flat surface portion 202, it is easier for the practitioner to grip the grip part 22. Furthermore, since the grip part 22 includes the first curved surface portion 204 and the second curved surface portion 206, it is even easier for the practitioner to grip the grip part 22.

Next, the knob 36 will be described. As shown in FIGS. 8 and 9, the knob 36 includes a finger placing portion 220 on which the practitioner's thumb can be placed, and a pair of finger rest portions 222 and 224 that is provided on both sides of the finger placing portion 220 in the direction B around the axis.

For example, the finger placing portion 220 is provided on a part of an outer surface of the knob 36 to be concave in a direction perpendicular to the insertion axis Ax. Further, the finger placing portion 220 is formed as a concavely curved surface portion along a convexly curved surface of a ball of the thumb so that the ball of the thumb is easily placed on the finger placing portion 220. The finger placing portion 220 is an example of a finger placing portion of the present invention.

For example, the finger rest portions 222 and 224 are provided on a part of the outer surface of the knob 36 to be convex in a direction perpendicular to the insertion axis Ax. Both side portions of the thumb placed on the finger placing portion 220 are in contact with the finger rest portions 222 and 224. The finger rest portions 222 and 224 are an example of finger rest portions of the present invention.

According to the knob 36 having such a configuration, since the knob 36 includes the finger placing portion 220 and the pair of finger rest portions 222 and 224, it is easy for the practitioner to rotationally operate the knob 36.

Further, in a case where the knob 36 is positioned at a middle position that is used as a reference of a position relative to the grip part 22 in the direction B around the axis as shown in FIGS. 7 to 10, the finger placing portion 220 of the operation unit 21 of this embodiment is provided at a position facing the first flat surface portion 200 in the direction of the insertion axis Ax. Specifically, the finger placing portion 220 is provided on an extension of the first flat surface portion 200 in the direction of the insertion axis Ax. According to this configuration, in a case where the practitioner grips the grip part 22, the base portion of the thumb is in contact with the first flat surface portion 200 of the grip part 22. Accordingly, the practitioner can place the thumb on the finger placing portion 220 of the knob 36 in a natural state without bending the thumb. Furthermore, since both side portions of the thumb are in contact with the pair of finger rest portions 222 and 224, an operating force in a case where the practitioner moves the thumb in a left-right direction (the Y(−) direction and the Y(+) direction in FIG. 8) can be efficiently transmitted to the knob 36. Accordingly, it is easy to rotationally operate the knob 36, so that operability in changing the visual field direction is improved.

Further, as shown in FIGS. 8 and 9, the first flat surface portion 200 includes a first index 226, and the finger placing portion 220 includes a second index 228. In a case where the knob 36 is positioned at the middle position, the first index 226 and the second index 228 are provided on a same line H extending in the direction of the insertion axis Ax. Accordingly, it is possible to easily align the rotational position of the knob 36 with the middle position by rotating the knob 36 relative to the grip part 22 in the direction B around the axis to align the first index 226 and the second index 228 with the same line H.

Furthermore, each of the first index 226 and the second index 228 is formed of a convex portion as shown in FIG. 9. Specifically, the first index 226 is formed of a convex portion protruding in the Z(+) direction from the first flat surface portion 200, and the second index 228 is formed of a convex portion protruding in the Z(+) direction from the finger placing portion 220. Since each of the first index 226 and the second index 228 is formed of a convex portion as described above, the practitioner can easily check the positions of the first index 226 and the second index 228 using visual observation and tactile sensation.

Moreover, each of the convex portions showing the first index 226 and the second index 228 is formed as a convex stripe portion formed along the same line H as shown in FIGS. 8 and 9. Since each of the first index 226 and the second index 228 is formed as a convex stripe portion formed along the same line H, it is easy to align the first index 226 and the second index 228 with the same line H.

Further, in a case where the knob 36 is positioned at the middle position that is the reference position, as shown in FIG. 7, the optical axis OA (see FIG. 2) extending in a direction inclined with respect to the insertion axis Ax includes a component corresponding to a direction that faces a side opposite to a normal direction to the first flat surface portion 200 indicated by an arrow J and is indicated by an arrow K. Accordingly, in a case where the insertion unit 20 is inserted into a body in a diagonally downward direction as viewed in the Y direction of FIG. 7 in a state where the knob 36 is positioned at the reference position, an image pickup direction is a diagonally downward direction that is inclined with respect to the diagonally downward direction by the inclination angle of the diagonally downward direction. That is, the reference position of the knob 36 is set to a position where the image pickup direction is a diagonally downward direction.

Furthermore, the knob 36 includes a third index 230 as shown in FIG. 10. The third index 230 is formed at a position different from the position of the second index 228 shown in FIGS. 8 and 9, and functions as an index that indicates a position relative to the grip part 22 in the direction B around the axis. For example, the third index 230 is formed on the outer surface of the knob 36 at a position on a side opposite to the second index 228 with the insertion axis Ax interposed between the second index 228 and the third index 230 (a position away from the second index 228 in the direction around the axis by an angle of 180°). The third index 230 is an example of a third index of the present invention.

Since such a third index 230 is provided on the knob 36, the following advantages are obtained. That is, in a case where the knob 36 is rotated relative to the grip part 22 from the middle position in the direction B around the axis by a large angle (for example, about 120°), the second index 228 may not be visually observed depending on the rotational position of the knob 36, and it may be difficult to ascertain the current rotation angle of the knob 36. Since the third index 230 away from the second index 228 in the direction B around the axis by an angle of 180° can be visually observed in this case, the rotational position of the knob 36 can be ascertained on the basis of the third index 230.

Further, the third index 230 is formed of a concave portion as shown in FIG. 10. Since the third index 230 is formed of a concave portion as described above, the third index 230 can be easily distinguished from the second index 228 formed as a convex portion. Furthermore, the concave portion showing the third index 230 is formed as a concave stripe portion formed in the direction of the insertion axis Ax. Since the third index 230 is formed as a concave stripe portion formed in the direction of the insertion axis Ax as described above, the rotational position of the knob 36 in a case where the practitioner views the third index 230 is easily ascertained.

Next, an action of the oblique-viewing endoscope 10 according to the embodiment will be described.

In the oblique-viewing endoscope 10 according to the embodiment, the practitioner grips the grip part 22 and inserts the insertion unit 20 into a patient's body and then rotationally operates the knob 36 in the direction B around the axis in a case where a visual field direction is to be changed. Then, the outer pipe 30 and the protection sheath 32 to be rotated integrally with the knob 36 are rotated in the same direction, and the visual field direction can be directed to a desired direction. Further, in a case where the practitioner rotationally operates the outer pipe 30 using the knob 36, the rotation (co-rotation) of the protection sheath 32 and the inner sheath 34 (the proximal end optical system 50 and the image pickup unit 60) in the direction B around the axis is prevented. That is, since the posture of the inner sheath 34 in the direction B around the axis is maintained by the magnet coupling 102, the rotation of an observation image to be observed on the monitor 16 is prevented even though the visual field direction is changed. As a result, the operability of the oblique-viewing endoscope 10 is improved.

In the oblique-viewing endoscope 10 according to the embodiment, it is easy to grip the grip part 22 since the base portion of the thumb is in contact with the first flat surface portion 200 of the grip part 22 in a case where the practitioner grips the grip part 22. Further, in a case where the palm of the right hand is turned up, the grip part 22 is prevented from rolling on the palm of the right hand since the second flat surface portion 202 is formed on the outer surface of the grip part 22. Accordingly, since the rotation of an observation image to be observed on the monitor can be prevented, the operability of the oblique-viewing endoscope 10 is improved.

Furthermore, in a case where the practitioner grips the grip part 22 in a state where the knob 36 is positioned at the middle position and the finger placing portion 220 faces the first flat surface portion 200 in the direction of the insertion axis Ax, the base portion of the practitioner's thumb is in contact with the flat surface of the first flat surface portion 200. Accordingly, the practitioner can place the thumb on the finger placing portion 220 of the knob 36 in a natural state without bending the thumb. Further, in a case where a visual field direction is to be changed, the practitioner rotationally operates the knob 36 in the direction B around the axis using the finger rest portions 222 and 224 that are in contact with both sides of the thumb. In this operation for changing the visual field direction, the practitioner can perform the operation for changing the visual field direction with the thumb of the hand gripping the grip part 22. Accordingly, in the operation for changing the visual field direction, the practitioner can perform the operation with one hand. As a result, it is easy to perform an operation for changing the visual field direction.

According to the endoscope of the embodiment, as described above, the grip part 22 includes the first flat surface portion 200 formed in the direction of the insertion axis Ax on a part of the outer surface of the grip part 22, the knob 36 includes the finger placing portion 220 and the pair of finger rest portions 222 and 224, and the finger placing portion 220 faces the first flat surface portion 200 in the direction of the insertion axis Ax in a case where the knob 36 is positioned at the middle position (reference position). Accordingly, operability in changing the visual field direction is improved.

Further, in a case where the practitioner grips the grip part 22, four fingers (particularly, the middle finger and the ring finger) other than the thumb are in contact with the second flat surface portion 202 of the grip part 22. Accordingly, since the practitioner can reliably grip the grip part 22 using the thumb being in contact with the first flat surface portion 200 and four fingers other than the thumb being in contact with the second flat surface portion 202, the gripping property of the grip part 22 is significantly improved.

Furthermore, since the palm of the hand is in contact with the first curved surface portion 204 (second curved surface portion 206) of the grip part 22, a sense of stability in a case where the practitioner grips the grip part 22 is improved. As a result, in a case where the practitioner grips the grip part 22, the practitioner can stably hold the grip part 22 in the palm (substantially the entire portion excluding five fingers) of the hand.

Examples of the endoscope according to the embodiment of the present invention have been described above, but the present invention may include some improvements or modifications without departing from the scope of the present invention.

EXPLANATION OF REFERENCES

10: oblique-viewing endoscope
12: endoscope system
14: processor device
16: monitor
18: light source device
20: insertion unit
21: operation unit
22: grip part
24: camera unit
26: first signal cable
27: second signal cable
28: light guide
28C: light emitting end
30: outer pipe
31: space

32: protection sheath
34: inner sheath
36: knob
38: seal ring
40: distal end optical system
42: distal end portion body
44: distal end lens barrel
45: tubular portion
46: cover glass
48*a*: objective lens
48*b*: prism
48*c*: lens
50: proximal end optical system
52: proximal end lens barrel
54: holder
55: prism
56: lens
60: image pickup unit
64: image pickup element
66: circuit board
68: connector
70: light guide-insertion space
72: external cable
74: case
80: sealed space
82: airtight connector
84: connecting unit
90: connection member
92: bearing receiving member
94: bearing
96: bearing receiving member
98: bearing
100: connecting beam
100*a*: ring portion
100*b*: ring portion
102: magnet coupling
103: first magnet
104: second magnet
120: rotation stopper
122: stopper groove
122*a*: groove portion
122*b*: wall portion
122*c*: wall portion
124: stopper pin
200: first flat surface portion
200A: side edge portion
200B: side edge portion
202: second flat surface portion
202A: side edge portion
202B: side edge portion
204: first curved surface portion
206: second curved surface portion
207: distal end portion
208: proximal end portion
208A: bulging portion
220: finger placing portion
222: finger rest portion
224: finger rest portion
226: first index
228: second index
230: third index
Ax: insertion axis
OA: optical axis
B: direction around axis
C: diagonally right-downward direction
D: central axis of rotation
F: counterclockwise direction
G: clockwise direction
H: same line
J: arrow
K: arrow

What is claimed is:

1. An endoscope comprising:

an insertion unit including an optical system at a distal end thereof and that is rotatable in a direction around an insertion axis;

an image pickup unit configured to pick up an image of light passing through the optical system; and an operation unit that is connected to a proximal end side of the insertion unit, wherein the operation unit includes:

a grip part that extends in a direction of the insertion axis; and a rotational operation member that is provided between the grip part and the insertion unit, is adapted to be rotatable relative to the grip part, and rotates the insertion unit in the direction around the insertion axis, the grip part includes a first flat surface portion that is formed along the insertion axis on a part of an outer surface of the grip part, and the first flat surface portion includes a surface perpendicular to a vertical direction of an image formed from image pickup signals output from the image pickup unit and is configured to receive a base portion of a finger of a practitioner who grips the grip part, the rotational operation member includes:

only one finger placing portion on which the finger is placeable; and a pair of finger rest portions that is provided on both sides of the only one finger placing portion in the direction around the insertion axis, and is configured to protrude from the only one finger placing portion and receive an operating force in the direction around the insertion axis from the finger, and the only one finger placing portion is provided on an extension of the first flat surface in the direction of the insertion axis and is provided at a position facing the first flat surface portion in the direction of the insertion axis in a case where the rotational operation member is positioned at only one reference position used as a reference of a position relative to the grip part in the direction around the insertion axis.

2. The endoscope according to claim 1, wherein the first flat surface portion is formed over a proximal end portion from a distal end portion of the grip part in the direction of the insertion axis.

3. The endoscope according to claim 1, wherein the first flat surface portion includes a first index, the only one finger placing portion includes a second index, and the first index and the second index are provided on a same line extending in the direction of the insertion axis in a case where the rotational operation member is positioned at the only one reference position.

4. The endoscope according to claim 3, wherein the first index and the second index are convex portions.

5. The endoscope according to claim 4, wherein the convex portion is a convex stripe portion formed along the same line.

6. The endoscope according to claim 1, wherein the grip part includes a second flat surface portion parallel to the first flat surface portion and formed on the outer surface of the grip part at a position on a side opposite to the first flat surface portion with the insertion axis interposed between the first flat surface portion and the second flat surface portion.

7. The endoscope according to claim 3, wherein the rotational operation member includes a third index formed at a position different from a position of the second index and indicating a position relative to the grip part in the direction around the insertion axis.

8. The endoscope according to claim 7, wherein the third index is a concave portion.

9. The endoscope according to claim 8, wherein the concave portion is a concave stripe portion formed in the direction of the insertion axis.

10. The endoscope according to claim 1, wherein the rotational operation member is adapted to be rotatable between a first rotational position and a second rotational position relative to the grip part in the direction around the insertion axis, and the only one reference position is a middle position between the first rotational position and the second rotational position.

11. The endoscope according to claim 1, wherein the surface of the first flat surface portion is formed, on the outer surface of the grip part, at a position indicating a top side in the vertical direction of the image that is a direction indicating a top and a bottom of the image.

12. The endoscope according to claim 1, wherein an image pickup direction of the image pickup unit is a direction inclined with respect to the insertion axis, and the image pickup direction of the image pickup unit includes a component corresponding to a direction that faces a side opposite to an outward normal direction to the first flat surface portion in a case where the rotational operation member is positioned at the only one reference position.

13. The endoscope according to claim 1, wherein the insertion unit includes:

an outer pipe, a protection sheath that is inserted into the outer pipe, is provided with the optical system at a distal end thereof, and is rotatable integrally with the outer pipe in the direction around the insertion axis of the insertion unit, and an inner sheath that is inserted into the protection sheath, is provided with the image pickup unit at a distal end thereof, and is rotatable relative to the protection sheath in the direction around the insertion axis.

* * * * *